United States Patent [19]
Sergio et al.

[11] Patent Number: 6,092,649
[45] Date of Patent: Jul. 25, 2000

[54] CARTRIDGE FOR HOLDING A FIRST AND SECOND FLUID

[75] Inventors: Roberto M. Sergio, Jenkintown; Winfield Wood, Jr., Gywnedd, both of Pa.; Peter O. Sildye, GlenEllyn, Ill.

[73] Assignee: Sermed Industries Inc., Abington, Pa.

[21] Appl. No.: 09/425,263

[22] Filed: Oct. 22, 1999

Related U.S. Application Data

[60] Provisional application No. 60/105,221, Oct. 22, 1998, provisional application No. 60/105,115, Oct. 22, 1998, and provisional application No. 60/105,225, Oct. 22, 1998.

[51] Int. Cl.[7] .................................................. B65D 25/08
[52] U.S. Cl. ........................... 206/222; 206/568; 141/330; 215/DIG. 8; 222/83.5
[58] Field of Search .................................. 206/219–222, 206/568; 141/105, 106, 330; 215/6, 10, DIG. 8; 222/81, 83, 83.5, 88; 422/100, 102, 104, 292, 294

[56] References Cited

U.S. PATENT DOCUMENTS

| | | | |
|---|---|---|---|
| 3,655,096 | 4/1972 | Easter ........................................ | 206/222 |
| 3,840,136 | 10/1974 | Lanfranconi et al. .................... | 222/83.5 |
| 3,964,640 | 6/1976 | Laughlin .................................. | 141/330 |
| 4,446,989 | 5/1984 | Brannen .................................... | 222/81 |
| 4,752,444 | 6/1988 | Bowen et al. . | |
| 5,008,079 | 4/1991 | Wutzler et al. . | |
| 5,029,718 | 7/1991 | Rizzardi .................................... | 206/222 |
| 5,037,623 | 8/1991 | Schneider et al. . | |
| 5,048,723 | 9/1991 | Seymour .................................. | 141/330 |
| 5,077,008 | 12/1991 | Kralovic et al. . | |
| 5,225,160 | 7/1993 | Sanford et al. . | |
| 5,348,711 | 9/1994 | Johnson et al. . | |

FOREIGN PATENT DOCUMENTS

3239549 A1  4/1984  Germany .

*Primary Examiner*—Paul T. Sewell
*Assistant Examiner*—Luan K. Bui
*Attorney, Agent, or Firm*—Akin, Gump, Strauss, Hauer & Feld, L.L.P.

[57] ABSTRACT

A cartridge for holding a first and a second fluid including an outer capsule containing the first fluid. An inner capsule is enclosed within the outer capsule and has a portion attached to a portion of an inner surface of the outer capsule. The inner capsule contains the second fluid. A self-sealing preferable section is disposed on the outer capsule and a perforatable section is disposed on the inner capsule and is generally aligned with the self-sealing perforatable section of the outer capsule. The concentration of the second fluid in the inner capsule increases the shelf life of the second fluid, relative to the shelf life of the mixture of the first fluid and the second fluid, while the outer capsule and the first fluid act as a protective layer to cause the second fluid to be mixed with the first fluid to form a non-hazardous mixture in the event of an accidental rupture of the inner capsule, thus increasing the variety of fluids, and their associated shelf lives, that can be stored or transported. In the alternative, the present invention is directed to a base unit for receiving a cartridge having an outer capsule containing a first fluid and enclosing an inner capsule containing a second fluid. The base unit includes a body having a recess that receives the cartridge. A perforating tube is disposed in the recess of the body and has a distal end adapted to perforate the outer capsule and to perforate the inner capsule. The perforating tube has at least one opening displaced from the distal end for removing the mixture of the first fluid and the second fluid from the cartridge. In the alternative the present invention is directed to a system for mixing a first fluid and a second fluid including the above cartridge and base unit.

13 Claims, 3 Drawing Sheets

6,092,649

CARTRIDGE FOR HOLDING A FIRST AND SECOND FLUID

CROSS-REFERENCE TO RELATED APPLICATIONS

This application claims priority from U.S. Provisional Patent Application No. 60/105,221 entitled, "Cartridge Assembly for Sterilant Containment" filed Oct. 22, 1998, and is hereby incorporated by reference herein in its entirety. This application also claims priority from U.S. Provisional Patent Application No. 60/105,115 entitled, "Method and Apparatus for the Sterilization of Dental Handpieces at Room Temperature" filed Oct. 22, 1998, which is hereby incorporated by reference herein in its entirety. This application also claims priority from U.S. Provisional Patent Application No. 60/105,225 entitled, "Apparatus for the Sterilization of Threaded Areas of Dental Handpieces" filed Oct. 22, 1998, which is hereby incorporated by reference herein in its entirety.

BACKGROUND OF THE INVENTION

The present invention relates to a cartridge which facilitates the transport and storage of a mixture and, more specifically, relates to a cartridge for holding and mixing a first and a second fluid.

Chemical sterilization is often preferable when an object being sterilized is thermosensitive and prone to wear when subjected to high temperatures. However, the use of a suitable mixture for sterilization is often complicated by difficulties incurred during the transport and storage of the components of the mixture.

For example, once the various components of a mixture for sterilization are combined, the shelf life of the overall mixture is often fairly limited. Limited shelf lives require that the mixture be used soon after the actual time when the various components were mixed. This reduces the usefulness of chemical sterilization as only limited amounts of a sterilizing mixture can be distributed for use because of the inability of end users to store the mixture for a reasonable length of time due to the limited shelf life.

One alternative to shipping the pre-mixed mixture is to ship the various components separately. While this often overcomes the difficulties associated with the limited shelf life of the resulting mixture of the component, other difficulties develop when shipping the various components of the mixture separately. For example, when shipping concentrated component solutions, special packing and shipping procedures may need to be followed due to the potentially hazardous nature of various components of the mixture when they are in a more concentrated and undiluted form. Additionally, the mixing of the various components by users requires that extra safety precautions be taken to prevent injury to the personnel that prepare the mixture. Moreover, when personnel are relied upon to properly measure and combine various components of the mixture, errors in the resulting mixture often occur.

Accordingly, the use of chemical sterilization currently presents many difficulties. As discussed above, some of the problems that are inherent in using chemical sterilization include the need for specialized shipping procedures, limited shelf life, inability to store the mixture for extended periods of time, hazards presented to personnel who mix the various components, and errors in mixing the separate components in the proper amounts.

What is currently needed in the chemical sterilization art is a device for shipping the various components of a mixture in a manner that does not require additional safeguards or special shipping procedures, that maintains the shelf life of the various components of the mixture to allow for reasonable storage periods, and that simplifies the mixing of the components to allow personnel to safely and easily mix the various components while preventing errors due to the mixing of improper amounts of the various components.

SUMMARY OF THE INVENTION

Briefly stated, the present invention is directed to a cartridge for holding a first and a second fluid including an outer capsule containing the first fluid. An inner capsule is enclosed within the outer capsule and has a portion attached to a portion of an inner surface of the outer capsule. The inner capsule contains the second fluid. A self-sealing preferable section is disposed on the outer capsule and a perforatable section is disposed on the inner capsule generally aligned with the self-sealing perforatable section of the outer capsule. The concentration of the second fluid in the inner capsule increases the shelf life of the second fluid, relative to the shelf life of the mixture of the first fluid and the second fluid, while the outer capsule and the first fluid act as a protective layer to cause the second fluid to be mixed with the first fluid to form a non-hazardous mixture in the event of an accidental rupture of the inner capsule, thus increasing the variety of fluids, and their associated shelf lives, that can be stored or transported.

The present invention is alternatively directed to a base unit for receiving a cartridge having an outer capsule containing a first fluid and enclosing an inner capsule containing a second fluid. The base unit includes a body having a recess that receives the cartridge. A perforating tube is disposed in the recess of the body, the tube having a distal end adapted to perforate the outer capsule and to perforate the inner capsule. The perforating tube has at least one opening displaced from the distal end for removing the mixture of the first fluid and the second fluid from the cartridge.

The present invention is alternatively directed to a system for mixing a first fluid and a second fluid. The system includes a cartridge having an outer capsule containing the first fluid and an inner capsule enclosed within the outer capsule and attached to a first end of the outer capsule. The inner capsule contains the second fluid. A self-sealing perforatable section is disposed on the outer capsule and a perforatable section is disposed on the inner capsule generally aligned with the self-sealing perforatable section of the outer capsule. The outer capsule and the first fluid act as a protective layer causing the second fluid to be mixed with the first fluid to form a non-hazardous mixture of the first fluid and the second fluid in the event of an accidental rupture of the inner capsule. The system includes a base unit having a body, which has a recess for receiving the cartridge. A perforating tube is disposed in the recess, the tube having a distal end for perforating the self-sealing perforatable section of the outer capsule and the perforatable section of the inner capsule when the cartridge is inserted into the recess. The perforating tube is adapted to remove a mixture of the first fluid and the second fluid from the cartridge after the perforating tube has perforated the outer capsule and the inner capsule.

BRIEF DESCRIPTION OF THE SEVERAL VIEWS OF THE DRAWINGS

The foregoing summary, as well as the following detailed description of the preferred embodiment of the invention, will be better understood when read in conjunction with the appended drawings. For the purpose of illustrating the invention, there is shown in the drawings an embodiment, which is presently preferred. It is understood, however, that the invention is not limited to the precise arrangement and instrumentality shown. In the drawings.

DETAILED DESCRIPTION OF THE INVENTION

Figure 1:
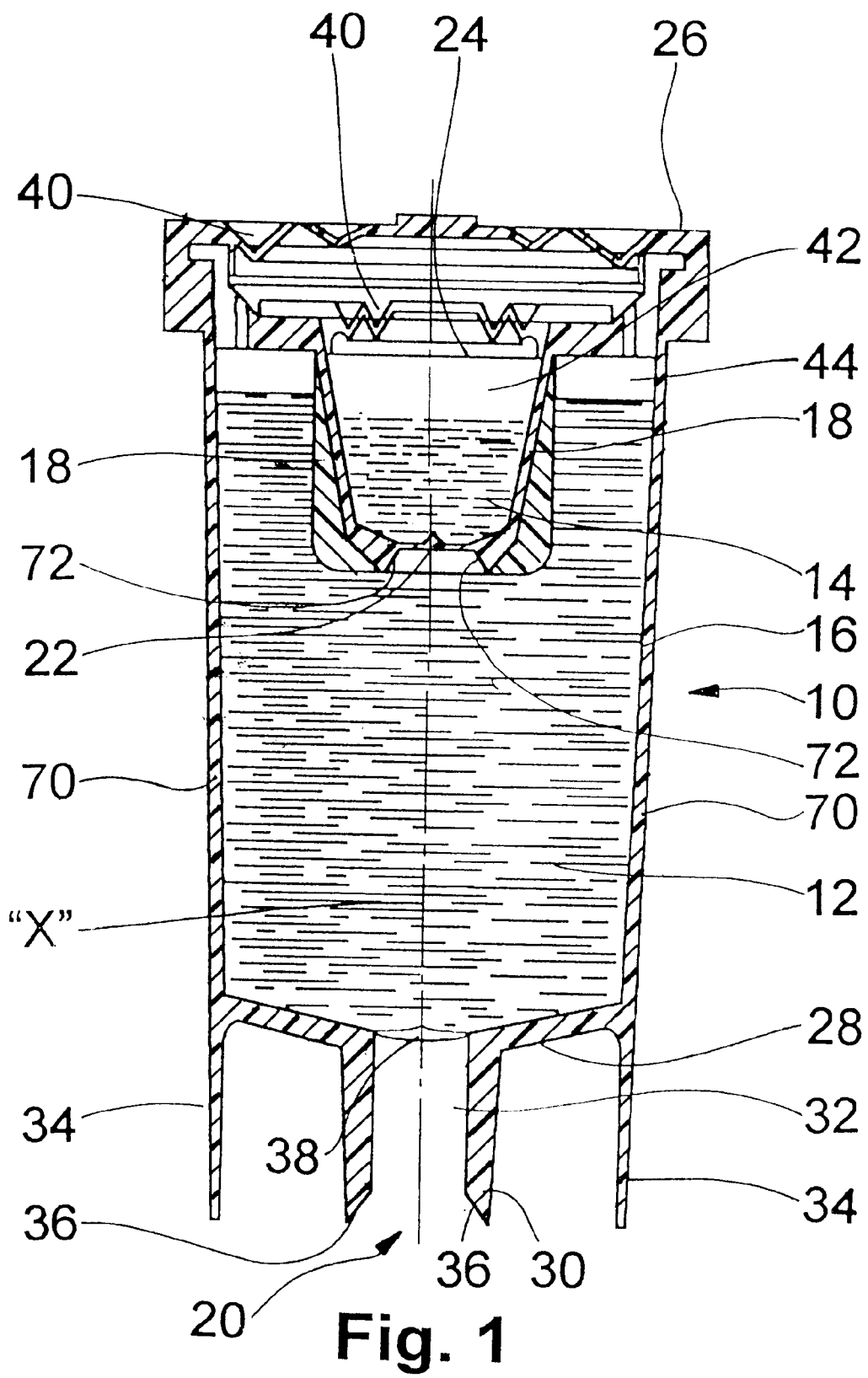
FIG. 1 is an enlarged elevational cross-sectional view of a cartridge according to a preferred embodiment of the present invention.

Certain terminology is used in the following description for convenience only and is not limiting. The words "right," "left," "lower," and "upper" designate directions in the drawings to which reference is made. The words "inwardly" and "outwardly" refer to directions toward and away from, respectively, the geometric center of the system for mixing a first fluid and a second fluid and designated parts thereof. The terminology includes the words above specifically mentioned, derivatives thereof, and words of similar import. Additionally, the word "a," as used in the specification and in the claims, means "at least one."

Figures 2, 3:
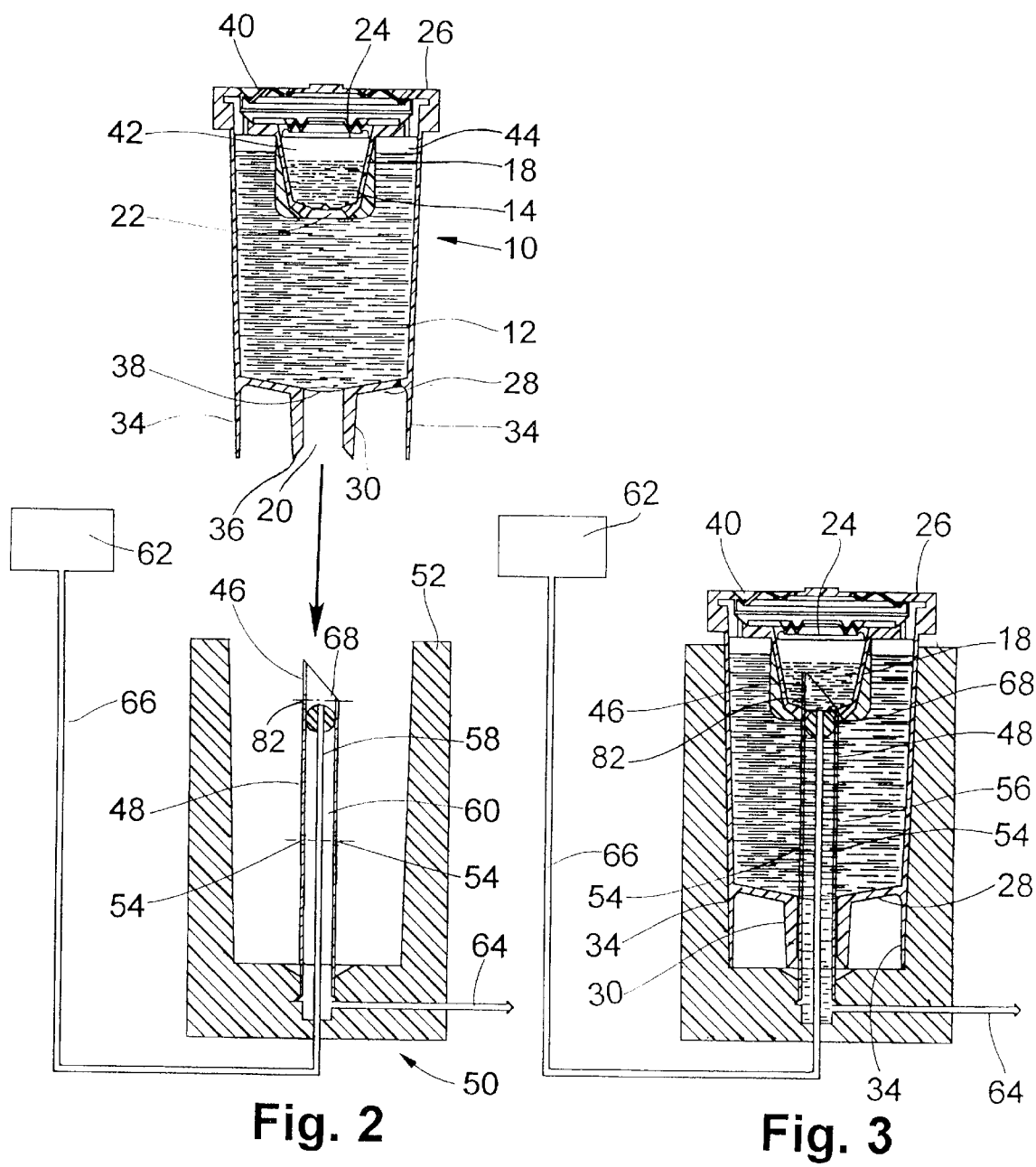
FIG. 2 is an elevational cross-sectional view of a system for mixing a first and second fluid including the cartridge of FIG. 1 and a base unit according to a preferred embodiment of the present invention.
FIG. 3 is an elevational cross-sectional view of the system of FIG. 2 illustrating the removal of a mixture of the first and second fluids from the cartridge by the base unit.
Figure 4:
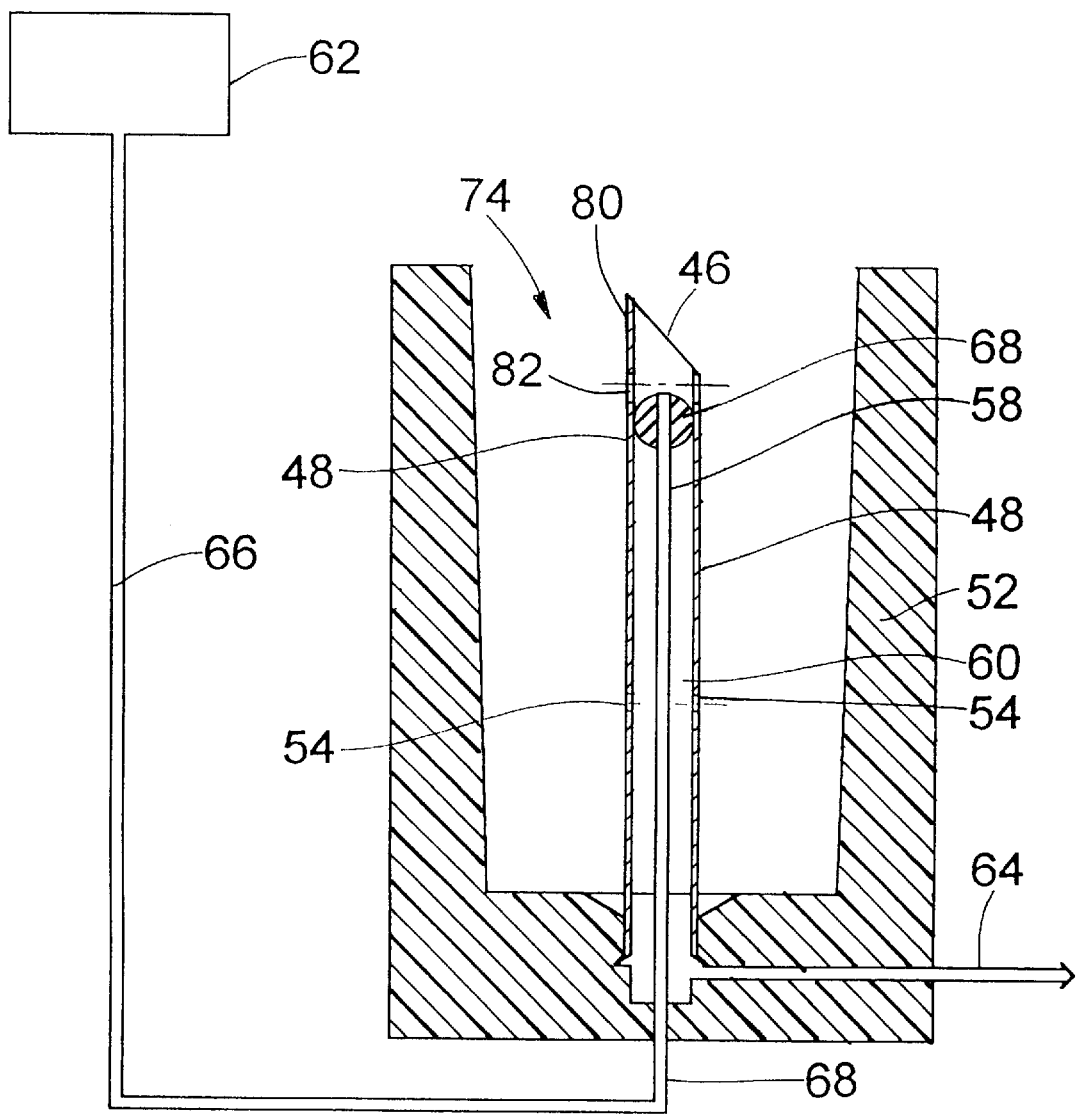
FIG. 4 is an enlarged elevational cross-sectional view of the base unit of FIG. 2.

Referring to the drawings in detail, wherein like numerals indicate like elements throughout, there is shown in FIGS. 1–3 a preferred embodiment of a cartridge, generally designated 10, and there is shown in FIGS. 2–4 a preferred embodiment of a base unit, generally designated 50. The cartridge 10 encloses and keeps separate a first fluid 12 and a second fluid 14. The concentration of the second fluid 14 in an inner capsule 18 increases the shelf life of the second fluid 14, relative to the shelf life of a mixture of the first fluid 12 and the second fluid 14, while an outer capsule 16 and the first fluid 12 act as a protective layer to cause the second fluid 14 to be mixed with the first fluid 12 to form a non-hazardous mixture 56 in the event of an accidental rupture of the inner capsule 18. Thus, the cartridge 10 increases the variety of fluids, and associated shelf lives, that can be stored or transported. A base unit 50 receives the cartridge 10 which has the outer capsule 16 containing the first fluid 12 and encloses the inner capsule 18 containing the second fluid 14. The base unit 50 is adapted to remove a mixture 56 of the first fluid 12 and the second fluid 14 from the cartridge 10.

Referring to FIGS. 1–3, the cartridge 10 for holding a first and second fluid 12, 14 includes the outer capsule 16 which contains the first fluid 12. The cartridge 10 preferably has a cylindrical shape when viewed along a longitudinal axis denoted "X" in FIG. 1. However, those of skill in the art will appreciate from this disclosure that the shape of the cartridge 10 as viewed along the longitudinal axis "X" can be varied without departing from the scope of the present invention. For example, the cartridge 10 can have a square shape, an oblong shape, or the like without departing from the present invention. Markings 40 on a first end 26 of the cartridge 10 are the result of the mechanical processes used to produce the cartridge 10. Accordingly, the markings 40 do not constitute a part of the present invention and thus, will not be further discussed herein. The cartridge 10 is preferably formed by spin welding the tops of the outer capsule 16 and the inner capsule 18. However, those of skill in the art will appreciate from this disclosure that various methods can be used to seal the cartridge 10 without departing from the scope of the present invention.

The first fluid is preferably sterilized water which is used to dilute the second fluid 14 in the case of an accidental rupture of the inner capsule 18. However, those of ordinary skill in the art will appreciate from this disclosure that other fluids can be used depending on the specific mixture being generated using the cartridge 10.

While the cartridge 10 shown in FIGS. 1–3 has a preferential height versus width ratio that is generally shown in the drawings, those of skill in the art will appreciate from this disclosure that the height versus width ratio of the cartridge 10 can be varied without departing from the scope of the present invention. Accordingly, a cartridge 10 can be produced that, when viewed in cross-section, appears to generally have the shape of a square, a triangle, or the like.

The cartridge 10 is preferably formed of a sturdy, non-reactive material, such as a polymer or the like. In the present invention the cartridge 10 is preferably formed of a polyethylene material. The outer surface 70 of the cartridge 10 generally tapers inward while moving from the first end 26 of the cartridge 10 toward the second end 28 of the cartridge 10. However, those of skill in the art will appreciate from this disclosure that the particular tapering of the outer surface 70 of the cartridge 10 is not critical to the present invention and that the outer surface 70 can be adjusted to taper outwards, to taper inwards to a greater degree, or to have no taper without departing from the scope of the present invention.

The inner capsule 18 is enclosed within the outer capsule 16 and has a portion attached to a portion of an inner surface of the outer capsule 16. The inner capsule 18 contains the second fluid 14. The second fluid 14 is preferably a concentrated peracetic acid. However, those of ordinary skill in the art will appreciate from this disclosure that other fluids can be used as the second fluid 14 depending on the particular mixture that is desired. Referring to FIGS. 1–3, the end 24 of the inner capsule 18 is attached proximate to the first end 26 of the outer capsule 16. While a preferred relative size ratio between the inner capsule 18 and the outer capsule 16 is shown, those of skill in the art will appreciate that the relative sizes of the inner capsule 18 and the outer capsule 16 can be varied provided that the outer capsule 16 encloses the inner capsule 18 and, in combination with the first fluid 12, provides a protective layer surrounding the inner capsule 18. Thus, if the inner capsule 18 is broken the concentrated peracetic acid is released into the sterilized water. The sterilized water then dilutes the concentrated peracetic acid to a non-hazardous level. Accordingly, the protective layer provided by the outer capsule 16 and the sterilized water 12 allows the concentrated peracetic acid to be shipped without having to use special shipping procedures By shipping the peracetic acid 14 in a concentrated form as a separate component, the shelf life of the peracetic acid 14 is increased.

While the preferred embodiment of the present invention uses one inner capsule 18 that is enclosed within the outer capsule 16 to allow for the easy mixing of the first and the second fluids 12, 14, those of skill in the art will appreciate from this disclosure that multiple inner capsules 18 can be used without departing from the scope of the present invention. For example, a third capsule can be positioned inside of the inner capsule 18 to allow for a mixture comprising three separate fluids which can be stored separately until the time of use at a patient-side location. In a similar vein, four, or more fluids can be contained by the cartridge 10 in capsules that are each stored within another capsule to provide for complicated mixtures which can be easily generated at a patient-side location.

A self-sealing perforatable section 20 is disposed on the outer capsule 16. The self-sealing perforatable section 20 includes a thin portion 38 which is preferably centrally located on the second end 28 of the cartridge 10. The thinner portion 38 of the second end 28 of the cartridge 10 allows a perforating tube 48 to penetrate the cartridge 10 as further detailed below.

The perforating tube 48 is preferably formed of inconnel. However, those of ordinary skill in the art will appreciate from this disclosure that the perforating tube 48 may be formed of another stainless steel, composite, alloy, or like materials having suitable low absorption and anti-corrosive properties.

The self-sealing perforatable section 20 of the outer capsule 16 includes an elongated tubular member 30 which extends outwardly from approximately the perimeter of the thinner portion 38 of the self-sealing perforatable section 20. It is preferable that the lower end of the elongated tubular member 30 have beveled edges 36 to facilitate the smooth insertion of the perforating tube 48 into the elongated tubular member 30. The beveled edges 36 of the elongated tubular member 30 cause the elongated tube to expand while the perforating tube 48 is inserted therein. The diameter of the elongated tubular member 30 is preferably slightly less than the diameter of the perforating tube 48. This causes the inner surface of the elongated tubular member to form a tight interference fit with the outer surface of the perforating tube 48 which prevents fluid from leaking out of the cartridge.

The elongated tubular member 30 facilitates the proper alignment of the perforating tube 48 with the thinner portion 38 of the second end 28 of the cartridge 10. The elongated tubular member 30 preferably tapers inwardly as the member 30 extends downwardly from the second end 28 of the cartridge 10 to grip the sides of the perforating tube 48 and to prevent leakage of fluids from the cartridge 10, as further detailed below.

A perforatable section 22 is disposed on the inner capsule 18 and is preferably generally aligned with the self-sealing perforatable section 20 of the outer capsule 16. A thinner walled portion of the inner capsule 18 preferably forms the perforatable section 22. The perforatable section preferably has beveled edges 72 which extend downwardly and outwardly from the lower portion of the inner capsule 18 to facilitate the insertion of the perforating tube 48 into the inner capsule 18. The beveled edges 72 preferably flare outwardly when moving from the top portion of the beveled edges 72 downwardly toward the second end 28 of the outer capsule 16 to facilitate the insertion of the perforating tube 48 and to ensure leakage of the second fluid 14 past the perforatable section 22 and into the first fluid 12.

It is preferable, but not necessary, that the outer and inner capsules 16, 18 each have a respective portion 40, 42 that is void of liquid. This allows the liquids to expand when subjected to heat during shipping without increasing the pressure of the liquid inside the outer and inner capsules 16, 18 beyond a predetermined pressure level.

While it is preferable that the perforatable section 22 and the self-sealing perforatable section 20 are generally aligned centrally in the cartridge 10, those of skill in the art will appreciate from this disclosure that the general positioning of the perforatable section 22 and the self-sealing perforatable section 20 is not critical to the present invention. Accordingly, the positioning of the self-sealing perforatable section 20 and the perforatable section 22 can be moved rightwardly, leftwardly, inwardly, and outwardly without departing from the scope of the present invention. One important aspect of the perforatable section 22 and the self-sealing perforatable section 20 is that they are generally aligned to allow the perforating tube 48 to perforate both the outer capsule 16 and the inner capsule 18.

While the preferred embodiment of the cartridge 10 has one inner capsule 18 and one self-sealing perforatable section 20 positioned on the second end 28 of the outer capsule 16, those of skill in the art will appreciate from this disclosure that multiple inner capsules 18 can be positioned proximate to the first end 26 of the outer capsule 20 and multiple self-sealing perforatable sections 20 can be positioned along the second end 28 of the outer capsule 16 to allow users to selectively mix a combination of fluids depending upon the particular mixture desired without departing from the scope of the present invention. Thus, a user would insert the perforating tube 28 into the self-sealing perforatable section 20 that corresponds to the particular inner capsule 18 containing the fluid which the user wishes to mix with the first fluid 12. Thus, the cartridge 10 of the present invention makes it possible to ship multiple fluids and allow a user to select the particular combination that would be mixed at a patient-side location.

As mentioned above, the cartridge 10 is perforated by a perforating tube 48 which is inserted into the cartridge 10 to remove fluids therefrom. To position the perforating tube 48, it is preferable to insert the cartridge 10 into a base unit 50. The base unit 50 includes a body 52 which has a recess 74 that receives the cartridge 10. The base unit 50 includes a bottom end 76 with a surrounding wall 78 which projects upwardly from the top side of the bottom end 76. The base unit 50 is preferably formed of polyethylene tetrachloride, however, those of ordinary skill in the art will appreciate from this disclosure that any material can be used to form the base unit 50 which has suitable low absorption and anti-corrosive properties.

The wall 78 extends preferably circularly around the perforating tube 48 to correspond to the shape of the cartridge 10. However, those of skill in the art will appreciate from this disclosure that various shapes can be formed about the recess 74 to facilitate the insertion of the cartridge 10 into the recess 74 without departing from the scope of the present invention. The sidewall 78 preferably increases in thickness when moving from the top end of the wall 78 toward the bottom of the wall 78 which causes the recess 74 to taper inwards. This increases the ease with which the cartridge 10 can be properly inserted into the recess 74.

The perforating tube 48 is disposed in the recess 74 of the body 50. Referring to FIGS. 2–4, the perforating tube 48 is preferably generally centrally aligned in the bottom end 76 of the base unit 50. The positioning of the perforating tube 48 corresponds to the positioning of the self-sealing perforatable section 20 and the perforatable section 22. Depending upon the position of the self-sealing perforatable section 20 and the perforatable section 22 of the cartridge 10, the position of the perforating tube 48 can be adjusted within the recess to allow the perforating tube 48 to align with the self-sealing perforatable section 20 and the perforatable section 22. Thus, when multiple self-sealing perforatable sections 20 are used to allow a user to selectively mix one of multiple fluids contained in multiple inner capsules 18 with the first fluid 12 contained in the outer capsule 16, the user simply adjusts the positioning of the perforating tube 48 prior to insertion of the cartridge 10 into the base unit 50 to generate the preferred mixture.

The perforating tube 48 preferably has a generally cylindrical shape, however, those of skill in the art will appreciate that the particular shape of the perforating tube 48 can be altered without departing from the scope of the present invention. The perforating tube 48 preferably has a distal end 46 adapted to perforate the outer capsule 16 and to perforate the inner capsule 18.

The distal end 46 of the perforating tube 48 is preferably angled to produce a point 80 which forms the initial tear in each of the self-sealing perforatable sections 20 and perforatable sections 22 to facilitate the insertion of the perforating tube 48 into the outer capsule 16 and into the inner capsule 18. While it is preferable that the perforating tube 48 have a distal end 46 which is cut in an angular fashion to form a point 80, those of skill in the art will appreciate from this disclosure that various other shapes and methods can be used for facilitating the insertion of the distal end 46 into the outer capsule 16 and into the inner capsule 18. For example, a V-shape can be cut into the distal end 46 of the perforating tube 48 to generate multiple points 80 which can be simultaneously inserted into the self-sealing perforatable section 20 and into the perforatable section 22.

The perforating tube 48 has at least one opening and preferably two or more openings 54 displaced from the distal end 46 of the perforating tube 48 for removing a mixture 56 of the first fluid 12 and the second fluid 14 from the cartridge 10. The opening 54 is positioned at a height along the perforating tube 48 such that after the cartridge 10 is fully inserted into the recess 74 and the perforating tube 48 has penetrated both the outer capsule 16 and the inner capsule 18, the opening 54 is positioned inside of the outer capsule 16 but outside of the inner capsule 18. Thus, when the perforating tube 48 is fully inserted into the cartridge, the openings 54 are positioned above the elongated tubular member 30 to prevent the openings from being sealed by the elongated tubular member 30. While it is preferable that the opening 54 be positioned proximate to the second end 28 of the outer capsule 16, those of skill in the art will appreciate from this disclosure that the opening 54 can be positioned anywhere along the perforating tube 48 without departing from the scope of the present invention as long as a mixture of the first and the second fluids 12, 14 can be collected through the opening 54.

An inner tube 58 is disposed within the perforating tube 48 and forms a channel 60 therebetween. While it is preferable that the inner tube 58 is generally centrally aligned within the perforating tube 48, those of skill in the art will appreciate that the precise positioning of the inner tube 58 can be adjusted without departing from the scope of the present invention. It is preferable that the inner tube 58 have a cylindrical shape, however, those of skill in the art will appreciate from this disclosure that the inner tube 58 can have any shape provided that the mixture 56 can flow freely within the channel 60.

While a preferred ratio between the size of the inner tube 58 and the perforating tube 48 is shown, those of skill in the art will appreciate that the relative size between the inner tube 58 and the perforating tube 48 can be adjusted without departing from the scope of the present invention provided that a channel 60 is maintained therebetween to facilitate the removal of the mixture 56. The channel 60 is preferably sealed proximate to the distal end 46 of the perforating tube 48. The channel 60 is preferably sealed by a stopper 68. The stopper 68 is preferably formed of a low absorption non-corrosive material such as polymer, composite, rubber, or the like.

An air filter 62 preferably, but not necessarily, has a fluid connection 66 to the base unit 50 and supplies filtered, unpressurized air to the cartridge 10 via the inner tube 58 for simplifying the removal of the second fluid 14 and the first fluid 12 from the cartridge 10. The air filter is preferably a hydrophobic filter that only allows gases to pass through while preventing the transfer of fluids. Those of skill in the art will understand from this disclosure that the air filter 62 can be replaced by a pump to supply pressurized air to the cartridge 10.

When the perforating tube 48 is inserted into the outer capsule 16, some sterilized water 12 may enter the inner tube 58. However, any sterilized water 12 that enters the inner tube is prevented from leaking out of the base unit by the hydrophobic filter 62. Then, when the perforating tube is inserted into the inner capsule 18, concentrated peracetic acid may also enter the inner tube 58. However, the peracetic acid is also prevented from leaking out of the base unit by the hydrophobic filter 62. Once the perforating tube 48 has broken the perforatable section 22 of the inner capsule 18, the second fluid (preferably peracetic acid) escapes from the inner capsule 18 and rapidly mixes with the first fluid (preferably sterilized water) 12. The rapid mixture of the second fluid 14 with the first fluid 12 upon the breaking of the perforatable section 22 is partially due to the slight positive pressure that exists in the inner capsule 18 due to the natural breakdown of the peracetic acid which is the preferred second fluid 14.

To facilitate the proper insertion of the perforating tube 48 into the cartridge 10, the cartridge 10 preferably has an annular support 34 extending outwardly from the second end 28 of the outer capsule 16 for controlling the degree of insertion of the cartridge 10 into the recess 74. The support 34 preferably extends downwardly from the perimeter of the second end 28 of the cartridge 10. Thus, the support 34 preferably forms a tube-like chute that allows the cartridge 10 to be stored in an upright position.

The base unit 50 also includes a conduit 64 which is attached to the channel 60 for removing the mixture 56 of the first fluid 12 and the second fluid 14 from the base unit 50. The conduit 64 is attached to the bottom end of the perforating tube 48 and is used to supply the mixture 56 to the apparatus or process which includes the use of the mixture 56. This system of the present invention which includes the base unit 50 and the cartridge 10 is preferably intended for use with a sterilizing apparatus such as that described in co-pending U.S. Patent Application entitled "An Apparatus and Method for Sterilizing an Instrument," which was filed Oct. 22, 1999, and is hereby incorporated by reference herein its entirety. Once the mixture 56 is being supplied to the apparatus (not shown) via the conduit 64, air is drawn into the cartridge 10 through the hydrophobic filter 62 which causes any fluid which entered the inner tube 58 when the perforating tube 48 was inserted into the cartridge 10 to be pushed out of the inner tube 58.

The system for mixing a first fluid 12 and a second fluid 14 according to the present invention includes the above-mentioned cartridge 10 and the above-mentioned base unit 50. The cartridge 10 uses multiple capsules to enclose multiple fluids which can be removed from the cartridge 10 by a perforating tube 48. The base unit 50 includes such a perforating tube 48 which is adapted to remove a mixture 56 of the first fluid 12 and the second fluid (or other fluids) 14 from the cartridge 10 after the perforating tube 48 has perforated the outer capsule 16 and the inner capsule 18.

Referring to FIGS. 1–4, the system of the present invention operates as follows. A cartridge 10 is removed from a storage location where the cartridge 10 was maintained in an upright position due to the preferably generally rigid annular support 34 which extends downward from the second end 28 of the outer capsule 16 forming a cylindrical supporting tube. Then, while holding the cartridge 10 in an upright position, the cartridge 10 is positioned above the recess 74 of the base unit 50 so that the desired self-sealing perforatable section 20 is aligned with the perforating tube 48. As mentioned above, depending upon the number of inner capsules 18, the selection of a specific self-sealing perforatable section 20 can result in the generation of a particular desired mixture 56.

Then, the cartridge 10 is inserted into the recess 74 while guiding the elongated tubular member 30 over the perforating tube 48 and bringing the tip 80 of the perforating tube 48 into contact with the thinner portion 38 of the self-sealing perforatable section 20. As the tip 80 presses against the thinner portion 38 of the self-sealing perforatable section 20, a tear is made in the thinner portion 38 which facilitates the insertion of the perforating tube 48 into the outer capsule 16. Once the perforating tube 48 is inserted within the outer capsule 16, the inward taper of the elongated tubular member 30 prevents leakage of fluid between the elongated tubular member 30 and the outer surface of the perforating tube 48.

Then, the cartridge 10 is further inserted into the recess 74 of the base unit 50 causing the tip 80 of the perforating tube 48 to contact the perforatable section 22 of an inner capsule 18 which is generally aligned with the self-sealing perforatable section 20 through which the perforating tube 48 is inserted. As the point 80 of the perforating tube 48 contacts the perforatable section 22, the point 80 forms a tear in the perforatable section 22 causing the second fluid 14 to flow between the outer surface of the perforating tube 48 and the inner surface of the beveled edges 72.

A through hole 82 is preferably positioned in the perforating tube 48 proximate to the top of the stopper 68 to prevent the second fluid 14 from becoming trapped in the portion of the perforating tube that extends upwardly past the stopper 68. Thus, in addition to the second fluid 14 flowing between the outer surface of the perforating tube 48 and the inner surface of the perforating section 22, some of the second fluid 14 flows into the perforating tube 48, through the through hole 82, along the outer surface of the perforating tube 48 and outside of the inner capsule 18.

The through hole 82 simplifies the insertion of the perforating tube 48 into the inner capsule by preventing the upper portion of the perforating tube 48 from increasing the pressure of the second fluid 14 more than necessary prior to the flow of the second fluid 14 from the inner capsule 18 into the outer capsule 16. The reduced compression caused by the through hole 82 in the perforating tube 48 simplifies the insertion of the perforating tube 48 into the inner capsule 18. When the perforating tube 48 initially perforates the perforatable section 22, portions of the perforatable section 22 act as a partial seal against the outer surface of the perforating tube 48 for a short period of time. Thus, by allowing the second fluid 14 to pass through the through hole 82 in the perforating tube prior to the beginning of the flow of the second fluid 14 along the outer surface of the perforating tube 48 some of the second fluid 14 can exit the inner capsule 18 via the through hole 82.

While it is preferable that the perforating tube has a through hole 82, those of skill in the art will appreciate from this disclosure that the through hole 82 is not necessary to the present invention. For example, the through hole 82 can be replaced with a single hole (not shown) extending through only one side of the perforating tube 48 or the through hole 82 can be eliminated altogether without departing from the scope of the present invention.

To facilitate the mixing of the second fluid 14 with the first fluid 12, the inner capsule 18 is maintained at a slightly positive pressure prior to the insertion of the perforating tube 48 therein. As mentioned above, the slight positive pressure is due to the natural breakdown of the second fluid 14. This pressure provides a force that helps expel the second fluid 14 out of the inner capsule 18 and encourages the second fluid 14 to mix with the first fluid 12.

The second fluid 14 is prevented from entering the channel 60 by the stopper 68 which is positioned between the inner tube 58 and the perforating tube 48. Once the first and second fluid 12, 14 are mixed, the mixture 56 is removed from the cartridge 10 via the at least one opening 54 which allows the mixture 56 into the channel 60. Then, the mixture flows out of the perforating tube 48 and into a conduit 64 which guides the desired mixture 56 to the appropriate application or apparatus. While it is preferable that a system of the present invention is used with a sterilizing apparatus, those of skill in the art will appreciate from this disclosure that the system of the present invention can be used with any apparatus or method which requires the mixing of multiple fluids.

It is recognized by those skilled in the art that changes may be made to the above-described embodiment of the invention without departing from the broad inventive concept thereof. It is understood, therefore, that this invention is not limited to the particular embodiment disclosed, but is intended to cover all modifications which are within the spirit and the scope of the invention as defined by the appended claims.

What is claimed is:

1. A cartridge for holding a first and a second fluid, comprising:
   an outer capsule containing the first fluid;
   an inner capsule enclosed within the outer capsule and having a portion attached to a portion of an inner surface of the outer capsule, the inner capsule containing the second fluid;
   a self sealing perforatable section disposed on the outer capsule; and
   a perforatable section disposed on the inner capsule and generally aligned with the self sealing perforatable section of the outer capsule, whereby the concentration of the second fluid in the inner capsule increases the shelf life of the second fluid, relative to the shelf life of a mixture of the first fluid and the second fluid, while the outer capsule and the first fluid act as a protective layer to cause the second fluid to be mixed with the first fluid to form a non hazardous mixture in the event of an accidental rupture of the inner capsule, thus increasing the variety of fluids, and associated shelf lives, that can be stored or transported.

2. The cartridge of claim 1, wherein an end of the inner capsule is attached proximate to a first end of the outer capsule.

3. The cartridge of claim 2, further comprising a support extending from a second end of the outer capsule.

4. The cartridge of claim 3, wherein the self sealing perforatable section of the outer capsule includes an elongated tubular member extending outwardly from approximately the perimeter of the self sealing perforatable section.

5. A base unit for receiving a cartridge having an outer capsule containing a first fluid and enclosing an inner capsule containing a second fluid, the base unit comprising:
   a body having a recess that receives the cartridge;
   a perforating tube disposed in the recess of the body, the perforating tube having a distal end adapted to perforate the outer capsule and to perforate the inner capsule;
   the perforating tube having at least one opening displaced from the distal end for removing a mixture of the first fluid and the second fluid from the cartridge; and
   an inner tube disposed within the perforating tube forming a channel therebetween, the channel being sealed proximate to the distal end of the perforating tube.

6. The base unit of claim 5, further comprising an air filter having a fluid connection to the base unit and capable of supplying filtered air to the cartridge via the inner tube simplifying the removal of the mixture from the cartridge.

7. The base unit of claim 6, further comprising a conduit attached to the channel for removing the mixture of the first fluid and the second fluid from the base unit.

8. A system for mixing a first fluid and a second fluid, the system comprising:
   a cartridge including:
      an outer capsule containing the first fluid;
      an inner capsule enclosed within the outer capsule and attached proximate to a first end of the outer capsule, the inner capsule containing the second fluid;
      a self sealing perforatable section disposed on the outer capsule; and
      a perforatable section disposed on the inner capsule and generally aligned with the self sealing perforatable section of the outer capsule, whereby the outer capsule and the first fluid act as a protective layer causing the second fluid to be mixed with the first fluid to form a non hazardous mixture of the first fluid and the second fluid in the event of an accidental rupture of the inner capsule;
   a base unit including:
      a body having a recess for receiving the cartridge;
      a perforating tube disposed in the recess and having a distal end for perforating the self sealing perforatable section of the outer capsule and the perforatable section of the inner capsule when the cartridge is inserted into the recess; and
      the perforating tube being adapted to remove a mixture of the first fluid and the second fluid from the cartridge after the perforating tube has perforated the outer capsule and the inner capsule.

9. The system of claim 8, wherein the perforating tube includes at least one opening displaced from the distal end for removing the mixture of the first fluid and the second fluid from the cartridge.

10. The system of claim 8, wherein the cartridge has a support extending outwardly from a second end the outer capsule for controlling the degree of insertion of the cartridge into the recess.

11. The system of claim 8, wherein the self sealing perforatable section of the outer capsule includes an elongated tubular member extending outward for sealingly engaging the perforating tube.

12. The system of claim 8, wherein the base unit includes an inner tube disposed within the perforating tube forming a channel therebetween, the channel being sealed proximate the distal end of the perforating tube for preventing unmixed first fluid from entering the channel.

13. The system of claim 12, further comprising an air filter having a fluid connection to the base unit and supplying filtered air to the cartridge via the inner tube for facilitating the removal of the mixture from the cartridge.

* * * * *